US00PP14204P29

(12) United States Plant Patent
Oudshoorn

(10) Patent No.: US PP14,204 P2
(45) Date of Patent: Oct. 7, 2003

(54) MONARDA PLANT NAMED 'PINK SUPREME'

(50) Latin Name: *Monarda didyma L.*
Varietal Denomination: Pink Supreme

(75) Inventor: Hubertus Gerardus Oudshoorn, Rijpwetering (NL)

(73) Assignee: Future Plants V.O.F., Lisserbroek (NL)

( * ) Notice: Subject to any disclaimer, the term of this patent is extended or adjusted under 35 U.S.C. 154(b) by 0 days.

(21) Appl. No.: 10/139,966

(22) Filed: May 6, 2002

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM, Plant Variety Database, 2003/01, GTI Jouve Retrieval Software, Citation for Monarda 'Pink Supreme'.*

* cited by examiner

*Primary Examiner*—Bruce R. Campell
*Assistant Examiner*—June Hwu
(74) *Attorney, Agent, or Firm*—C. A. Whealy

(57) ABSTRACT

A distinct cultivar of Monarda plant named 'Pink Supreme', characterized by its upright, outwardly spreading and relatively short plant habit; freely flowering habit; and dark pink-colored flowers arranged in dense verticillasters.

1 Drawing Sheet

Botanical classification/cultivar designation: *Monarda didyma L.* cultivar Pink Supreme.

BACKGROUND OF THE INVENTION

The present Invention relates to a new and distinct cultivar of Monarda plant, botanically known as *Monarda didyma L.*, and hereinafter referred to by the cultivar name Pink Supreme.

The new Monarda originated from a chance cross-pollination of two unidentified selections of *Monarda didyma L.*, not patented. The new Monarda was discovered by the Inventor in 1995 in Rijpwetering, The Netherlands. Plants of the new Monarda differed primarily from plants of the unidentified parental selections in plant size and flower color.

Asexual reproduction of the new cultivar by cuttings in Rijpwetering, The Netherlands since 1995, has shown that the unique features of this new Monarda are stable and reproduced true to type in successive generations.

SUMMARY OF THE INVENTION

Plants of the cultivar Pink Supreme have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'Pink Supreme'. These characteristics in combination distinguish 'Pink Supreme' as a new and distinct cultivar:

1. Upright, outwardly spreading and relatively short plant habit.
2. Freely flowering habit.
3. Dark pink-colored flowers arranged in dense verticillasters.

Plants of the new Monarda can be compared to plants of the Monarda cultivar Twins, not patented. In side-by-side comparisons conducted in Rijpwetering, The Netherlands, plants of the new Monarda differed from of the cultivar Twins in the following characteristics:

1 . Plants of the new Monarda were shorter than plants of the cultivar Twins.
2. Plants of the new Monarda and the cultivar Twins differed in flower color.

BRIEF DESCRIPTION OF THE PHOTOGRAPH

The accompanying colored photograph illustrates the overall appearance of the new Monarda, showing the colors as true as it is reasonably possible to obtain in colored reproductions of this type. Colors in the photograph may differ slightly from the color values cited in the detailed botanical description which accurately describe the colors of the new Monarda. The photograph comprises a side perspective view of a typical flowering plant of 'Pink Supreme' grown in a container.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were about two years old and grown under outdoor field conditions which closely approximate commercial production conditions in Lisse, The Netherlands. The photograph and the description information were taken in August, 2001.

Botanical classification: *Monarda didyma L.* cultivar Pink Supreme.

Parentage: Cross-pollination of two unidentified selections of *Monarda didyma L.*, not patented.

Propagation:

*Type*.—By cuttings.

*Time to initiate roots*.—About 60 days at 18° C.

*Time to produce a rooted young plant*.—About 90 days at 18 to 20° C.

*Root description*.—Fine, fibrous, freely branching; white to light brown in color.

Plant description:

*Form*.—Perennial flowering shrub; upright and outwardly spreading plant habit; freely branching; moderately vigorous growth habit.

*Plant height*.—About 60 cm.

*Plant diameter*.—About 60 cm.

*Lateral branch description*.—Number per plant: About eight. Length: About 25 cm. Diameter: About 4 mm. Internode length: About 6 cm. Strength: Moderately strong. Texture: Sparsely pubescent. Color: 143B to 144A to 144B.

*Foliage description*.—Arrangement: Opposite, simple. Length: About 10 cm. Width: About 6.2 cm. Shape: Ovate. Apex: Apiculate. Base: Rounded to cordate. Margin: Serrate. Texture, upper and lower surfaces: Pubescent; slightly rugose. Venation pattern: Pinnate. Fragrance: When rubbed, spicy; typical of *Monarda didyma L*. Petiole: Length: About 1.5 cm. Diameter: About 2 mm. Texture: Pubescent. Color: Young foliage, upper surface: 137A. Young foliage, lower surface: 137C. Fully expanded foliage, upper surface: Slightly lighter than 139A. Fully expanded foliage, lower surface: 137C. Venation, upper surface: 143C. Venation, lower surface: 143C to 143D. Petiole, upper surface: 143B. Petiole, lower surface: 143C to 143D.

Flower description:

*Appearance*.—Single labiate flowers arranged in dense verticillasters. Flowers not persistent. Flowers face upward and outward.

*Quantity of flowers*.—About 80 flowers per verticillaster.

*Natural flowering season*.—Plants flower continuously from late July into early September in Lisse, The Netherlands.

*Fragrance*.—Spicy; typical of *Monarda didyma L.*

*Flower longevity*.—About five days.

*Verticillaster height*.—About 4 cm.

*Verticillaster diameter*.—About 7 cm.

*Flower diameter*.—About 8 mm.

*Flower depth* (*height*).—About 4 cm.

*Flower buds*.—Length: About 1.9 cm. Diameter: About 3 mm. Shape: Ovoid. Color: 58A.

*Corolla*.—Arrangement: Petals modified into two lips; upper lip erect, lower lip spreading and 2-lobed. Length, upper and lower lips: About 2.9 cm. Width, upper lip: About 3 mm. Width, lower lip: About 8 mm. Shape, upper lip: Lanceolate. Shape, lower lip: Oblong. Apex, upper lip: Acute. Apex, lower lip: Emarginate. Base, upper and lower lips: Fused. Margin, upper and lower lips: Entire. Texture, upper and lower surfaces: Pubescent. Color, upper and lower lips: When opening and fully opened, upper surface: N57A to N57B. When opening and fully opened, lower surface: N57B.

*Calyx*.—Arrangement: Five sepals fused; tubular. Sepal length: About 7 mm. Sepal width: About 3 mm. Sepal shape: Linear. Apex: Acuminate. Base: Fused. Margin: Entire. Texture, upper and lower surfaces: Pubescent. Color: When opening, upper and lower surfaces: 177A to 177B. Fully opened, upper and lower surfaces: 177C; towards apex, 177A to darker than 177A.

*Flower bracts*.—Arrangement: About seven leafy bracts subtend the verticillasters. Length: About 5 cm. Width: About 2.8 cm. Shape: Elliptic to rhomboidal. Apex: Acute. Texture, upper and lower surfaces: Pubescent. Color, upper surface: 137A to 143C; occasionally with a spot towards the base, N186C. Color, lower surface: 137C.

*Peduncles/pedicels*.—Flowers arranged directly on lateral branch terminals; not stalked.

*Reproductive organs*.—Stamens: Quantity per flower: About two. Anther shape: Narrowly oblong; dorsifixed. Anther length: About 2 mm. Anther color: 166A to 166B Pollen amount: Scarce. Pollen color: Close to 13A. Pistils: Quantity per flower: One. Pistil length: About 3 cm. Style length: About 2.9 cm. Style color: 77B; towards the base, lighter than 77B. Stigma shape: Cleft. Stigma color: 77A. Ovary color: Close to 144B.

*Fruit*.—Quantity per plant: About 80 per lateral branch. Length: About 0.3 mm. Diameter: About 0.3 mm. Texture: Smooth. Color: 200A.

*Seed*.—Quantity per fruit: One. Length: About 0.2 mm. Diameter: About 0.2 mm. Color: 200A.

Disease/pest resistance: Plants of the new Monarda have not been noted to be resistant to pathogens or pests common to Monarda.

Temperature tolerance: Plants of the new Monarda are tolerant to temperatures from about −30 to 40° C.

It is claimed:

1. A new and distinct cultivar of Monarda plant named 'Pink Supreme', as illustrated and described.

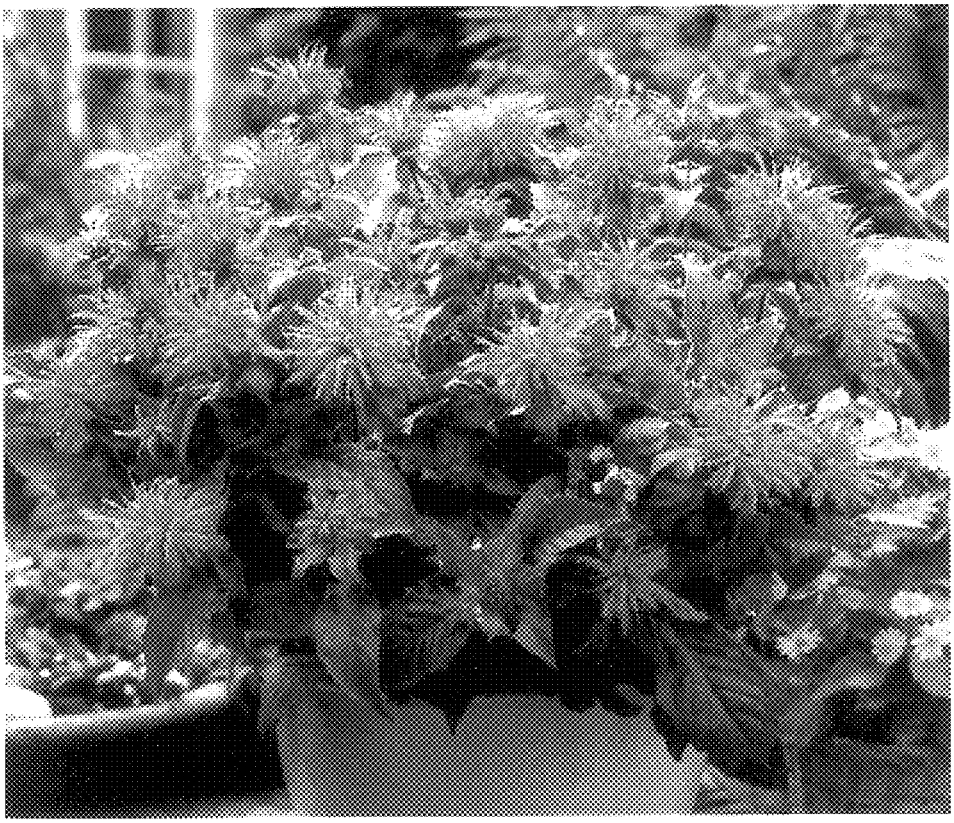

* * * * *